United States Patent [19]

Ma et al.

[11] Patent Number: 5,358,920
[45] Date of Patent: Oct. 25, 1994

[54] DEHYDROGENATING CATALYST FOR SATURATE HYDROCARBONS

[75] Inventors: Yongfu Ma; Peicheng Wu; Yong Sun; Sangjian Zhu; Yuexin Huang; Weiying Yang; Kaiwen Yao; Youreng Zou, all of Nanjing, China

[73] Assignees: China Petro-Chemical Corporation; Jing Ling Petrochemical Company, Sinopec, Beijing, China

[21] Appl. No.: 155,400

[22] Filed: Nov. 19, 1993

[30] Foreign Application Priority Data

Dec. 21, 1992 [CN] China .............................. 92114525.X

[51] Int. Cl.⁵ .................. B01J 23/78; B01J 21/04; B01J 35/08; C07C 5/333
[52] U.S. Cl. ...................... 502/330; 502/8; 585/660
[58] Field of Search ............... 502/330, 334, 8; 585/660

[56] References Cited

U.S. PATENT DOCUMENTS

| | | | |
|---|---|---|---|
| 2,620,314 | 12/1952 | Hockstra | 252/448 |
| 3,531,534 | 9/1970 | Adolph | 260/614 |
| 3,725,304 | 4/1973 | Wilhelm | 252/441 |
| 3,851,003 | 11/1974 | Wilhelm | 260/668 |
| 3,909,451 | 9/1975 | Wilhelm | 252/441 |
| 3,998,900 | 12/1976 | Wilhelm | 260/688 |
| 4,070,413 | 1/1978 | Imai | 260/683 |
| 4,430,517 | 2/1984 | Imai et al. | 585/660 |
| 4,608,360 | 8/1986 | Abrevaya et al. | 502/226 |
| 4,672,146 | 6/1987 | Abrevaya et al. | 585/660 |
| 4,677,237 | 6/1987 | Imai et al. | 585/444 |
| 4,717,779 | 1/1988 | Bricker et al. | 585/443 |
| 4,762,960 | 8/1988 | Imai et al. | 585/660 |
| 4,886,928 | 12/1989 | Imai et al. | 585/660 |
| 5,258,567 | 11/1993 | Kerby et al. | 585/660 |

FOREIGN PATENT DOCUMENTS 87101513A 10/1988 China .

OTHER PUBLICATIONS

Journal of Catalysis 101, 186–194 (1986), "Development of Carriers with controlled Concentration of Charged Surface Groups in Aqueous Solutions", L. Vordonis et al., pp. 187–195.

*Primary Examiner*—Paul E. Konopka
*Attorney, Agent, or Firm*—Pennie & Edmonds

[57] ABSTRACT

A dehydrogenating catalyst for saturated hydrocarbons comprising platinum, tin, sodium and $\tau$-alumina. The support of the catalyst is a large pore diameter $\tau$-$Al_2O_3$ with dual pore diameter distribution. At least 40% of the total pore volume is contributed by pores with pore diameter in the range of 1000–10000 Å. Platinum, tin, and sodium are impregnated onto support by co-impregnation method, followed by drying, calcinating, and steam-treating, as well as reducing by hydrogen, to prepare a long life dehydrogenating catalyst.

8 Claims, 1 Drawing Sheet

DEHYDROGENATING CATALYST FOR SATURATE HYDROCARBONS

The present invention relates to an improved dehydrogenating catalyst for saturated hydrocarbons. The present invention relates to a catalyst for the dehydrogenation of $C_6$–$C_{16}$ linear paraffins to prepare mono-olefins, and further to a process for the preparation for the same.

Dehydrogenating hydrocarbons is an important industrial conversion process. The dehydrogenation of hydrocarbons such as aliphatic paraffins and naphthene is used to prepare the raw materials for producing detergents, medical products, plastics, synthetic rubbers, and a variety of chemicals. The catalysts used for dehydrogenating hydrocarbons comprise mainly platinum as an active component, and tin, arsenic, cobalt, lead, germanium, thallium, indium, etc. as the second or third components Alkali metals such as lithium and potassium or alkaline earth metals such as calcium are used as promoters. The dehydrogenating catalysts described in U.S. Pat. Nos. 3,531,543, 3,725,304, 3,851,003, 3,909,451, and 4,070,413 comprises platinum, stannum, lithium and $\tau$-$Al_2O_3$, and are used for dehydrogenating linear $C_2$–$C_{30}$ paraffins.

The catalysts described in U.S. Pat. Nos. 3,998,900, 4,430,517, 4,608,360, and 4,677,237 comprise platinum as an active component, tin or indium as the second component, and lithium or potassium as the promoter. The catalyst disclosed in U.S. Pat. No. 3,998,900 comprises platinum, tin, lithium or potassium supported on $\tau$-$Al_2O_3$. Such catalysts are prepared by impregnating an aluminum oxide substrate with platinum and tin, calcining, then impregnating said substrate with lithium. The catalyst has to be presulfided by a mixed gas of $H_2S$ and $H_2$ before use. The support for the catalyst prepared according to the method described in U.S. Pat. No. 2,620,314, is a spherical bead of $\tau$-$Al_2O_3$ with medium pore diameter having a pore diameter distribution centered at about 300–500 Å. It is reported that optimum performance is obtained when said catalyst contains lithium or potassium.

The catalyst disclosed in U.S. Pat. No. 4,672,146 comprises platinum, tin, lithium (or potassium), and $\tau$-$Al_2O_3$ and contains chlorine and sulfur. Tin is introduced into the catalyst during the preparation of the $\tau$-$Al_2O_3$ support. The catalyst is used for dehydrogenation of $C_2$–$C_{30}$ paraffins.

The catalyst described in U.S. Pat. No. 4,762,960 comprises platinum as the active component, an element selected from tin, germanium, and/or rhenium as the second component, and lithium or potassium as the promoter. Platinum is provided on a support by a surface impregnation method. The average concentration of platinum in the outer 100 nm of the support is twice as much as the amount of platinum at a depth of 200 nm. The catalyst also contains chlorine and is used for the dehydrogenation of hydrocarbons.

The catalyst described in U.S. Pat. No. 4,886,928 comprises platinum as the active component, an element selected from scandium, yttrium, and actinium as the second component, an element selected from tin, lead, and germanium as the third component, and lithium or potassium as the promoter. The catalyst is used for dehydrogenation of hydrocarbons.

The catalyst provided by U.S. Pat. No. 4,717,779 is used for the dehydrogenation of ethyl benzene. In the catalyst described a Group VIII element and a Group IV element are the active component and the second component, and an alkali metal such as Li, Na, and K is included as the promoter. However, the patent does not indicate that the use of sodium as a promoter can improve the performance of the catalyst. There is no disclosure of the use of sodium as a promoter in the patent specification.

In Chinese Patent Application CN 87101513A, filed on Mar. 13, 1987, a catalyst comprised of platinum, tin, lithium, sulfur and $\tau$-$Al_2O_3$ is revealed. Platinum is used as the active component, tin as the second component, lithium as the promoter, and sulfur is used as an additional ingredient. The support of the catalyst has an average pore diameter greater than 200 Å. The catalyst is wet-sulfided using a sulfide as a sulfiding agent, and reduced by hydrogen before use. The reduced catalyst is used for the dehydrogenation of $C_3$–$C_{30}$ aliphatic hydrocarbons. The present invention is an improvement of the above mentioned invention.

Up to now, dehydrogenating catalysts reported by the prior art were all based on compositions including platinum as the active component, tin and the like as the second and third components, and lithium, potassium, or calcium as the promoter. These catalysts were reported to have good catalyst performance.

In summary, the catalysts described in the prior art do not contain sodium except for use as a promoter. The support provided by the prior art will have a detrimental effect on catalyst activity when sodium is used as promoter. For example, an article entitled "Development of Carriers with Controlled Concentration of Charged Surface Groups in Aqueous Solution" (Journal of Catalysis, 101, pp. 186–194, 1986) points out that sodium has a detrimental influence on the activity of supported catalysts. Hence, for a long time, sodium was never considered to be a good component for preparing catalyst promoter.

In addition, some prior art catalysts have to be sulfurized by sulfides before use in order to optimize the selectivity and stability of the catalyst. Moreover, the stability of those catalysts can not meet the requirements of newly developed dehydrogenation technology having high conversion rates.

The present invention provides a dehydrogenating catalyst for saturated hydrocarbons, especially for $C_6$–$C_{16}$ linear paraffins, which can be used to prepare linear mono-olefins. The catalyst has a high stability and can be used under severe operating conditions such as high temperature and low pressure, and does not need the sulfiding treatment for the conventional dehydrogenating catalyst before use.

The object of the present invention is to provide a catalyst comprising platinum as the active component, tin as the second component, large pore diameter $\tau$-$Al_2O_3$ with a dual pore diameter distribution as the support, and sodium as the promoter. The catalyst of this invention displays unexpectedly catalytic performance when compared with a catalyst using lithium as the promoter.

A further object of the present invention is to provide a supported catalyst which comprises platinum, tin, sodium, and $\tau$-$Al_2O_3$ to be used for the dehydrogenation of saturated hydrocarbons. The support for the catalyst of the present invention is prepared according to the method described in CN 87101513A. The spherical bead thus prepared is steam-treated to obtain a large pore diameter $\tau$-$Al_2O_3$ support. At least 40% of the total pore volume of the support is contributed by the pore diameter in the range of 1000–10000 Å. The catalyst is prepared by the co-impregnation of platinum, tin, and sodium on a spherical bead of $\tau$-$Al_2O_3$ support. The composition of the catalyst comprises 0.01–2.0% by weight of Pt, 0.01–5.0% by weight of Sn, 0.01–5.0% by weight of Na, and the remainder $\tau$-$Al_2O_3$ support.

The catalyst support of the present invention can be prepared by neutralizing an aqueous aluminum chloride solution containing from about 2% to about 10% $AlCl_3$ with ammonia water having a concentration of 1–10% ammonia at 60°–80° C. to a pH of 7.5–8.5. The resulting aluminum hydroxide solution is filtered and washed with water to a pH of 7, followed by washing with nitric acid to a pH of 3–6. The acidified slurry is formed into a bead in an oil ammonia column under pressure according to the method of CN 87101513A. The wet beads are washed with water, dried and calcined at 600°–800° C. for 1–10 hrs. The calcined beads are steam-treated with a steam-air mixture with a volume ratio of 10–100% at 600°–800° C. for 1–10 hrs. The pore diameter of the treated $\tau$-$Al_2O_3$ beads is measured using the pressurized mercury method. At least 40% of the total pore volume of the support is contributed by pores having a pore diameter in the range of 1000–10000 Å. The pore diameter distribution of the support is shown in FIG. 1.

Another object of the present invention is to provide a process for preparing a catalyst for the dehydrogenation of saturated hydrocarbons. Said process includes preparing a homogeneously mixed impregnation solution of chloroplatinic acid, stannous chloride, sodium chloride, ethyl alcohol, hydrochloric acid, and water. Ethyl alcohol and hydrochloric acid are present in the impregnation solution as 40–60% by volume and 3–8% by volume respectively. This solution is then impregnated on large pore diameter $\tau$-$Al_2O_3$ beads. The volume ratio of liquid to solid during impregnation is 0.5–2. After impregnation, the catalyst is dried, calcined at 400°–600° C. for 1–10 hours, and steam-treated for 1–10 hours by air containing steam. The content of steam in the air is 10–50% by volume during steam-treatment. The treated catalyst is further reduced using hydrogen having a water content of less than 20 ppm at 400°–600° C. for 5–20 hrs The product so obtained is the reduced catalyst used for the dehydrogenation of saturated hydrocarbons described as the invention.

The catalyst of the invention comprises; platinum, preferably in an amount of from about 0.2–1.0% by weight of composition; tin preferably in an amount of from about 0.2–1.5% by weight of composition; sodium in an amount of from about 0.1–1.5% by weight of composition; and large pore diameter $\tau$-$Al_2O_3$ bead support with a dual pore diameter distribution, wherein at least about 40% of the total pore volume is contributed by pores with a pore diameter in the range of 1000–10000 Å.

The support used for the dehydrogenating catalyst of the invention is an $\gamma$-type alumina. Metal components are supported on the surface of the support. The rate of dehydrogenation of hydrocarbons using the inventive catalyst is rather fast. Because the molecules of long chain paraffins are large, the rate of diffusion of the long chain paraffin molecules into the pores of the solid catalyst is rather slow. The dehydrogenation and carbon deposit reactions usually proceed in the catalyst pores. A catalyst having low density and large pore volume favors the diffusion of reactant molecules and the inhibition of carbon deposite. Hence, a large pore diameter support is preferred for the preparation of a catalyst according to the invention. However, large pore diameter supports can have poor catalyst strength and can cause catalyst crushing. The goal to be achieved in preparating a catalyst is to make the $\tau$-$Al_2O_3$ support possess not only large pore diameter but also high mechanical strength.

Although all the dehydrogenating catalysts use $\tau$-$Al_2O_3$ beads as support, the pore structure of the support differs with the different preparation technology. The preparation technology of $\tau$-$Al_2O_3$ support, i.e., the oil column bead shaping method using alumina sol described in U.S. Pat. No. 2,620,314, is used in all prior arts. The $\tau$-$Al_2O_3$ beads prepared by this method have a single pore distribution with pore diameter distribution concentrated in the 300–500 Å range. The limited pore diameter of this kind of support does not favor the dehydrogenating reaction. The support used for the catalyst of the present invention is prepared using an oil-ammonia column shaping method. The pore structure of the support, with a dual pore diameter distribution as indicated by the two peaks in the curve of pore diameter distribution (FIG. 1), is different from that of the support prepared using an oil column shaping method such as that described in U.S. Pat. No. 2,620,314. The pore diameter distribution of supports of the invention is primarily concentrated in two ranges: 75–100 Å for small pores and 2500–5000 Å for large pores. Use of this kind of the support having a dual pore diameter distribution containing a lot of large pores, favors dehydrogenation and enhances the strength of the support.

Because the support of the present invention has a dual pore diameter distribution having and at least 40% of the total pore volume contributed by pores having diameters in the range of 1000–10,000 Å, use of a sodium component supported on the support produces a catalyst possessing unexpectedly superior performance. Sulfidation is not necessary for the preparation and application of catalysts of according to the invention.

The catalyst of the invention exhibits high stability under severe conditions such as high temperature and low pressure. The catalyst is suitably used for the dehydrogenation of saturate hydrocarbons under severe conditions and is particularly suited for the dehydrogenation of $C_6$–$C_{16}$ linear paraffin to prepare linear mono-olefins. The sulfiding treatment for the conventional dehydrogenating catalysts is avoided.

Figure 1:
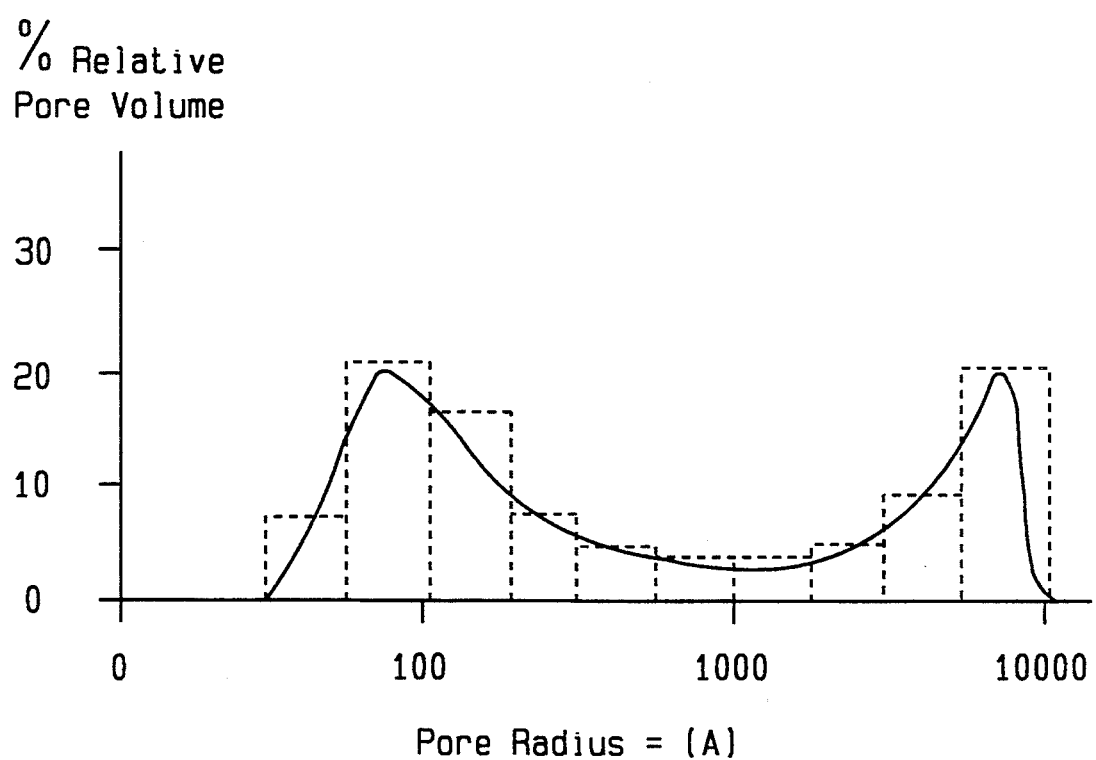
FIG. 1 is a pore diameter distribution curve of the $\tau$-$Al_2O_3$ bead support according to the present invention.

In order to exemplify the results achieved using the catalysts of the present invention, the following examples are provided without any intent to limit the scope of the invention to the discussion therein. All parts and percentages are by weight and all temperatures are in degrees celsius unless otherwise indicated.

EXAMPLE 1

The preparation of the $\tau$-$Al_2O_3$ bead support:

An aqueous solution of aluminum chloride containing 4% by weight $AlCl_3$ was neutralized using ammonia water containing 6% by weight of ammonia to a pH value of 7–8 at 65±5° C. thereby forming a solution of aluminium hydroxide. Said solution of aluminum hydroxide was filtered, washed with water to a pH of 7, and then acidified using nitric acid to a pH value of about 4–5 to form a slurry. After acidification, the slurry obtained was formed into beads according to the method of CN 87101513A. The wet beads were washed with water, dried, calcined at 700° C. for 4 hrs, and further treated at 700° C. using 50% by volume of a steam-air mixture for 15 hrs. The pore diameter of the steam-treated $\tau$-$Al_2O_3$ bead support was measured by the pressurized mercury method. At least 40% of the total pore volume was contributed by pores with pore diameters in the range of 10000–10,000 Å. The pore diameter distribution curve of the support is shown in FIG. 1.

EXAMPLE 2

The preparation of the catalyst: 328 ml aqueous chloroplatinic acid solution with a platinum content of 12.5 mg/ml, 187 ml aqueous stannous chloride solution with a tin content of 40 mg/ml, 220 ml aqueous sodium chloride solution with a sodium content of 25 mg/ml, 146.5 ml, 15% by weight of aqueous hydrochloric acid solution, and 1240 ml anhydrous ethyl alcohol were homogeneously mixed together to prepare an impregnation solution. 1000g of the $\tau$-$Al_2O_3$ bead support prepared in Example 1 was impregnated with the above prepared impregnation solution. After uniformly impregnating the bead support, the product was dried, calcined at 450°–500° C. for 4 hrs in a flowing air with gas volume hourly space velocity of 1500 $h^{-1}$, steam treated by 30% by volume of a steam-air mixture at 450°–500° C. for 4 hrs, dried and cooled by air, and reduced by hydrogen containing less than 20 ppm water with a gas-volume hourly space velocity of 1000 $h^{-1}$ at 450°–500° C. for 12 hrs. The catalyst (I) so prepared comprised 0.41% by weight of platinum, 0.748 % by weight of tin, and 0.55 % by weight of sodium.

EXAMPLE 3

Evaluation tests:

The evaluation of catalyst (I) prepared in Example 2 was conducted using $C_{10}$–$C_{13}$ linear paraffin with a sulfur content of less than 1 ppm as feed under a reaction condition of 0.1 MPa (gauge), inlet temperature 480° C., LHSV 20 $h^{-1}$ and H2/hydrocarbon mole ratio 5:1. The selectivity for converting paraffin to mono-olefins on catalyst (I) was 90%. The average conversion was 18.6%. The detailed results are listed in Table 1.

TABLE 1

| | The conversion level on catalyst (I). | | | | | | | | |
|---|---|---|---|---|---|---|---|---|---|
| | Time, length, h | | | | | | | | |
| | 8 | 16 | 24 | 32 | 40 | 56 | 64 | 72 | 86 |
| Conversion % | 22.4 | 21.1 | 19.8 | 19.5 | 19.1 | 17.6 | 17.2 | 16.4 | 14.8 |

EXAMPLE 4

Comparative test 1

Catalyst (I) of the invention comprised 0.41% by weight of platinum, 0.748% by weight of tin, and 0.55% by weight of sodium. Catalyst (II) comprised 0.41% by weight of platinum, 0.62% by weight of stannum, and 0.35% by weight of sodium which were supported on the $\tau$-$Al_2O_3$ beads prepared in Example 1. Catalyst (III) comprised 0.41% by weight of platinum, 0.50% by weight of tin, and 0.35% by weight of sodium which were supported on the $\tau$-$Al_2O_3$ beads prepared in Example 1. A hydrogenated $C_{10}$–$C_{13}$ linear paraffin with a sulfur content of less than 1 ppm was used as feed. The reaction condition were 0.1 MPa (gauge), inlet temperature 480° C., LHSV 20 $h^{-1}$, and a H2/hydrocarbon mole ratio of 5:1. The test duration was 90 hrs. The average conversion during the test period for catalyst (I), (II), and (III) were 18.6%, 18%, and 18% respectively. The selectivity was 90% for all the catalysts. The results of these tests indicate that the catalyst stability does not change with the change of tin and sodium contents.

EXAMPLE 5

Comparative test 2

Catalyst (I) of the invention comprised 0.41 by weight of platinum, 0.748% by weight of tin, and 0.55% by weight of sodium. Catalyst (A) (Chinese Patent Application CN 87101513A) comprised 0.375% by weight of platinum, 0.68% by weight of tin, and 0.48% by weight of lithium and was sulfided by wet method. A comparative test was performed to compare the performance of catalyst (I) and catalyst (A). A hydrogenated $C_{10}$–$C_{13}$ linear paraffin with a sulfur content of less than 1 ppm was used as feed. The reaction conditions were 0.1 MPa (gauge), inlet temperature 480° C. LHSV 20 $h^{-1}$, and H2/hydrocarbon mole ratio 5:1. The selectivity for converting paraffin to mono-olefin, on both catalyst (I) and catalyst (A) was 90%. The average conversion for catalyst (I) and catalyst (A) were 18.6% and 16.9% respectively. The detailed results are listed in Table 2.

TABLE 2

| | The comparison of conversion level between catalyst (I) and catalyst (A) | | | | | | | | | |
|---|---|---|---|---|---|---|---|---|---|---|
| | Time Length, h, | | | | | | | | | |
| | 8 | 16 | 24 | 32 | 40 | 48 | 56 | 64 | 72 | 86 |
| | | | | | Conversion, %, | | | | | |
| catalyst (1) | 22.4 | 21.1 | 19.8 | 19.5 | 19.1 | 19.1 | 17.8 | 17.2 | 16.4 | 14.8 |
| catalyst (A) | 22.1 | 19.6 | 19.4 | 18.4 | 17.6 | 17.0 | 15.5 | 14.4 | 14.2 | 11.8 |

The results of the comparative test of catalysts (I) and (A) show that, when both catalysts have the same selectivity of 90%, the conversion of catalyst (I) is higher than that of catalyst (A) (Chinese Patent Application CN 87101513A).

EXAMPLE 6

Comparative test 3

Catalyst (I) of the invention comprised 0.41% by weight of platinum, 0.748% by weight of tin, and 0.55% by weight of sodium. Catalyst (B) comprised 0.41% by weight of platinum, 0.748% by weight of tin, and 0.55% by weight of sodium. In catalyst (B), the support was the $\tau$-$Al_2O_3$ beads prepared by the method described in U.S. Pat. No. 3,998,900 and U.S. Pat. No. 2,620,314 (at least 90% of the total pore volume was contributed by the pores with a pore size less than 1000 A). A comparative test comparing the performance of catalyst (I) and catalyst (B). A hydrogenated $C_{10}$–$C_{13}$ linear paraffin with a sulfur content less than 1 ppm was used as feed. The reaction conditions were 0.1 MPa (gauge), inlet temperature 480° C., LHSV 20 h$^{-1}$, and $H_2$/hydrocarbon mole ratio 5:1. The selectivity for converting paraffin to mono-olefins on both catalyst (I) and catalyst (B) was 90%. The average conversion for catalyst (I) and catalyst (B) were 18.6 % and 15.7 % respectively. The results of the comparative test shows that the average conversion on catalyst (I) is higher than that on catalyst (B) although both catalysts have the same composition. The difference between catalyst (I) and catalyst (B) is that, large pore diameter $\tau$-$Al_2O_3$ beads were used as the support for catalyst (I) according to the invention while medium pore diameter $\tau$-$Al_2O_3$ beads with at least 90% pores having a pore diameter less than 1000 Å was used as the support for catalyst (B).

EXAMPLE 7

Comparative test 4

Catalyst (I) of the invention comprised 0.41% by weight of platinum, 0.748% by weight of tin, and 0.55% by weight of sodium. Catalyst (C) comprised 0.41% by weight of platinum, 0.748% by weight of tin, and 0.60% by weight of lithium. In catalyst (C), the support was large pore diameter $\tau$-$Al_2O_3$ beads prepared in Example 1. A comparative test was carried out too compare the performance of catalyst (I) and catalyst (C). A hydrogenated $C_{10}$–$C_{13}$ linear paraffin with a sulfur content of less than 1 ppm was used as feed. The reaction conditions were 0.1 MPa (gauge), inlet temperature 480° C. LHSV 20 h$^{-1}$, and an $H_2$/hydrocarbon mole ratio of 5:1. The selectivity for converting paraffin to mono-olefins on catalyst (I) and catalyst (C) were 90% and 89% respectively. The average conversion for catalyst (I) and catalyst (C) were 18.8% and 17.2% respectively. The results of this comparative test show that the average conversion on catalyst (I) is higher than that on catalyst (C) although both catalysts use the same support. The difference between catalyst (I) and catalyst (C) was that different promoters were used in catalyst (I) (platinum, tin, sodium/$\tau$-$Al_2O_3$ system) and catalyst (C) (platinum, tin, lithium/$\tau$-$Al_2O_3$ system).

EXAMPLE 8

Comparative test 5

Catalyst (I) of the invention comprised 0.41 by weight of platinum, 0.748% by weight of tin, and 0.55% by weight of sodium. Catalyst (A) (Chinese Patent Application CN 87101513A) comprised 0.375% by weight of platinum, 0.68 by weight of tin, and 0.48% by weight of lithium and was sulfided by wet method. Catalyst (D) (U.S. Pat. No. 3,909,451) comprised 0.370% by weight of platinum, 0.45% by weight of tin, and 0.48% by weight of lithium and the remainder $\tau$-$Al_2O_3$ support. Catalyst (E) (U.S. Pat. No. 4,608,360) comprised 0.40% by weight of platinum, 0.45% by weight of tin, 0.31% by weight of indium, and 0.45% by weight of lithium and the remainder $\tau$-$Al_2O_3$ support. A comparative test was performed for catalysts (I), (A), (D), and (E). A hydrogenated $C_{10}$–$C_{13}$ linear paraffin with a sulfur content less than 1 ppm was used as feed. The reaction conditions were 0.14 MPa (gauge), inlet temperature 482° C., LHSV 20 h$^{-1}$, and $H_2$/hydrocarbon mole ratio 6:1. The duration of the test was 500 hrs. The selectivity for converting paraffin to mono-olefins on all catalysts (I), (A), (D), and (E) was 85%. The average conversions for catalyst (I), (A), (D), and (E) were 18.2 13.4 11.3 and 13.3 respectively. The detailed results are listed in Table 3. The results of the comparative test indicate that the average conversion of the catalyst (I) of the invention is the highest of all the catalyst samples tested.

TABLE 3

The results of the comparative test for four different catalysts.

| Catalyst (related patent) | Selectivity, % | Conversion, % |
| --- | --- | --- |
| Catalyst (I) (the present invention) | 85 | 18.2 |
| Catalyst (A) (CN 87101513A) | 85 | 13.4 |
| Catalyst (D) (U.S. Pat. No. 3,909,451) | 85 | 11.3 |
| Catalyst (E) (U.S. Pat. No. 4,608,360) | 85 | 13.3 |

All patents, patent applications, and other publications appearing in this disclosure are herein incorporated by reference in their entirety. The scope of the following claims is intended to encompass all obvious changes in the details, materials, and arrangement of the parts that will occur to one of ordinary skill in the art:

What is claimed is:

1. A long life supported catalyst for use in dehydrogenating saturated hydrocarbons consisting essentially of 0.01–2.0% by weight of platinum, 0.01–5.0% by weight of tin, 0.01–5.0% by weight of sodium, and the remainder large pore diameter $\tau$-$Al_2O_3$ support, having a dual pore diameter distribution wherein at least 40% of the total pore volume is contributed by pores having a pore diameter in the range of 1000–10000 Å.

2. A catalyst for use in a dehydrogenation process according to claim 1, wherein the content of platinum is 0.2–1.0% by weight, the content of tin is 0.2–1.5% by weight, and the content of sodium is 1 to 1.5% by weight.

3. A catalyst for use in a dehydrogenation process according to claim 1, wherein the catalyst is used for the dehydrogenation of saturated hydrocarbons to prepare linear mono-olefins.

4. A catalyst of claim 3, wherein the saturated hydrocarbons are linear $C_6$–$C_{16}$ paraffin.

5. A process for preparing the catalysts of anyone of claims 1–2 and 4–5, which comprises the following steps;

(1) neutralizing a solution of aluminium tri-chloride with ammonia water, acidifying the obtained aluminium hydroxide sol with nitric acid, and forming the obtained slurry into spherical beads in an oil-ammonia column under pressure, followed by calcining at 600°–800° C. for 1–10 hrs, (2) steam-treating the calcined $\tau$-$Al_2O_3$ beads with a 10–100% by volume of steam-air mixture at 600°–800° C. for 1–20 hrs, (3) preparing an impregnation solution by mixing homogeneously chloroplatinic acid, stannous chloride, sodium chloride, hydrochloric acid, ethyl alcohol, and water.

(4) impregnating the $\tau$-$Al_2O_3$ beads prepared in step (2) with the impregnation solution prepared in step (3), drying and calcining said impregnated beads at a temperature of from about 400°–600° C. for 1–10 hrs, (5) further treating the product of step (4) with a 10–50% by volume of steam–air mixture at 400°–600° C. for 1–10 hrs, and (6) reducing the product of step (5) with hydrogen having a water content of less than 20 ppm at 400°–600° C. for 5–20 hrs.

6. A process of claim 5, wherein the liquid/solid volume ratio used for step (4) of the impregnation process is 0.5–2.

7. A process of claim 5, wherein the content of ethyl alcohol in the impregnation solution in step (3) is 40–60% by volume.

8. A process of claim 5, wherein the content of hydrochloric acid in the impregnation in step (3) is 3–8% by volume.

* * * * *